United States Patent
Desai

(10) Patent No.: US 9,012,432 B2
(45) Date of Patent: Apr. 21, 2015

(54) CO-ADMINISTRATION OF STEROIDS AND ZOLEDRONIC ACID TO PREVENT AND TREAT OSTEOARTHRITIS

(71) Applicant: Ketan Desai, Bethlehem, PA (US)

(72) Inventor: Ketan Desai, Bethlehem, PA (US)

(73) Assignee: Levolta Pharmaceuticals, Inc., Bethlehem, PA (US)

( * ) Notice: Subject to any disclaimer, the term of this patent is extended or adjusted under 35 U.S.C. 154(b) by 0 days.

(21) Appl. No.: 13/791,685

(22) Filed: Mar. 8, 2013

(65) Prior Publication Data

US 2014/0256681 A1 Sep. 11, 2014

(51) Int. Cl.
*A61K 31/60* (2006.01)
*A61K 31/663* (2006.01)
*A61K 31/683* (2006.01)
*A61K 31/573* (2006.01)

(52) U.S. Cl.
CPC .............. *A61K 31/683* (2013.01); *A61K 31/573* (2013.01); *A61K 31/663* (2013.01); *A61K 31/60* (2013.01)

(58) Field of Classification Search
CPC .............................. A61K 31/60; A61K 31/663
USPC .................................................... 514/94, 171
See application file for complete search history.

(56) References Cited

U.S. PATENT DOCUMENTS

| | | | |
|---|---|---|---|
| 2003/0195171 A1* | 10/2003 | Daifotis et al. | 514/89 |
| 2004/0063670 A1 | 4/2004 | Fox et al. | |
| 2005/0065117 A1* | 3/2005 | Lee | 514/89 |
| 2007/0048372 A1* | 3/2007 | Beyreuther et al. | 424/464 |
| 2009/0035315 A1* | 2/2009 | Christgau et al. | 424/145.1 |
| 2010/0158905 A1* | 6/2010 | Pearlman et al. | 424/133.1 |
| 2011/0263537 A1 | 10/2011 | Desai | |

OTHER PUBLICATIONS

Jul. 7, 2014 Notice of Allowance issued in U.S. Appl. No. 14/202,950 by Michael J. Schmitt.
Durnian, J., et al., "Bilateral acute uveitis and conjunctivitis after zoledronic acid therapy", "Eye (London)", Jul. 16, 2004, pp. 221-222, vol. 19, No. 2.
Jones, A., et al., "Intra-articular corticosteroids are effective in osteoarthritis but there are no clinical predictors of response", "Ann. Rheum. Dis.", 1996, pp. 829-832, vol. 55.
Di Lorenzo, G., et al., "Phase II Trial of Gemcitabine, Prednisone, and Zoledronic Acid in Pretreated Patients with Hormone Refractory Prostate Cancer", "Urology", 2007, pp. 347-351, vol. 69.
PDR 48th Edition, "Hydeltrason(R) Injection, Sterile (Prednisolone Sodium Phosphate), U.S.P.", "Physicians' Desk Reference", 1994, pp. 1460-1462.
Poznak, C., "The Use of Bisphosphonates in Patients With Breast Cancer", "Cancer Control", Nov./Dec. 2002, pp. 480-489, vol. 9, No. 6.
Unpublished U.S. Appl. No. 14/202,950, filed Mar. 10, 2014.
Laslett, L., et al., "Zoledronic acid reduces knee pain and bone marrow lesions over 1 year: a randomised controlled trial", "Ann Rheum Dis", Feb. 21, 2012, pp. 1322-1328, vol. 71.

* cited by examiner

*Primary Examiner* — Raymond Henley, III
(74) *Attorney, Agent, or Firm* — David Bradin

(57) ABSTRACT

A combination therapy for treating osteoarthritis is disclosed. The combination therapy includes the co-administration of a steroid and Zoledronic Acid. The coadministration of a steroid decreases the production of cytokines, and, therefore, decreases the pro-inflammatory effects of Zoledronic Acid. The co-administration of Zoledronic Acid with steroids treats osteoarthritis, and helps to prevent the onset of osteoarthritis in patients at risk for osteoarthritis.

15 Claims, No Drawings

CO-ADMINISTRATION OF STEROIDS AND ZOLEDRONIC ACID TO PREVENT AND TREAT OSTEOARTHRITIS

FIELD OF INVENTION

The present invention relates to the method of use for the co-administration of steroids and Zoledronic Acid to prevent and treat Osteoarthritis. The steroid administration can be oral, parenteral, inhalational, or by suppository. The invention also patents a composition of matter whereby 7.5 mg of Methyl Prednisolone is mixed with 4 or 5 mg of Zoledronic Acid and infused in Normal Saline.

BACKGROUND OF INVENTION

Zoledronic Acid, sold as Zometa/Aclasta/Reclast, is a nitrogen containing bisphosphonate that is used for treatment of hypercalcemia of malignancy, for the treatment of bone metastasis associated with malignancies such as prostate and breast cancer, for the prevention of and treatment of osteoporosis and for the treatment of Paget's disease.

Zoledronic Acid is administered by an intravenous infusion of 4 mg every 3-4 weeks (Zometa) for multiple myeloma and bone metastasis of other malignancies or 5 mg once a year (Aclasta/Reclast) for non-oncology indications. It is also used for the treatment of hypercalcemia of malignancy as needed.

Administration of Zoledronic Acid is complicated by what is described as "post-dosing syndrome" (PDS) which affects as much as 44% of patients as described in the Zometa Prescribing Information (http://www.pharma.us.novartis.com/product/pi/pdf/Zometa.pdf). The syndrome is characterized by fever, nausea, bone pain, arthralgia, myalgia, chills, etc. In addition, administration of Zoledronic Acid leads to worsening of arthralgia in persons suffering from osteoarthritis as described in Aclasta/Reclast/Zometa Prescribing Information.

The etiology of this phenomenon has not been identified, but is associated with an increase in levels of tumor necrosis factor (TNF), interleukin 6 (IL-6), and gamma interferon (γIFN) (Dicuonzo G et al 2003, Schweitzer D H et al 1995, Thiebaud D et al 1997). These cytokines are usually produced by T cells.

Zoledronic acid can cause stimulation of a subset of T cells known as gamma delta (γδ) T cells (Mariani S et al 2005). These cells, specifically V γ9/V γ2 T cells, can constitute up to 10% of circulating CD3 T cells when stimulated.

Upon stimulation by Zoledronic Acid, these γδT cells produce interleukin 2 (IL-2) and TNF. IL-2 in turn can stimulate the production of other cytokines such as IL-6 and γIFN. Thus, treatment with Zoledronic Acid can stimulate a subset of T cells that may lead to post-dosing syndrome by production and release of pro-inflammatory cytokines.

It would be advantageous to have compositions and methods for avoiding the onset of post-dosing syndrome. The present invention provides such compositions and methods.

Osteoarthritis (OA) is the most common bone and joint disease influenced by genetic and environmental factors. Osteoarthritis is a debilitating disorder, affecting millions of patients a year. Many therapeutics used to treat osteoarthritis have to be given on a daily basis, and in some cases, many times a day, in order to provide relief. The continued administration of these therapeutic agents, including non-steroidal anti-inflammatory drugs (NSAIDS), can result in liver disorders and gastro-intestinal perforations over time. In addition, they can cause impairment of renal function. Other measures to treat OA include direct injection into the knee joint of hyaluronic acid which causes relief for three to six months. It cannot be used in any other joint except the knee joint. Intra-articular steroids are used to treat OA, but they have a transient effect and are ineffective when given by any route other than by the intra-articular route. Thus, oral, intravenous, rectal, inhaled and topical steroids are not useful for treatment of OA. All intra-articular therapies have the side effect of pain during injection and possibilities of joint infection. All these medications treat pain, but do not have any effect on the disease.

Thus, there is no disease modifying agent to treat OA.

It would be advantageous to provide additional treatments for osteoarthritis, which can be given less frequently, have fewer side effects, and be effective. Finally, a disease modifying drug would be very useful.

In addition to those patients identified as suffering from osteoarthritis, there are also patients that are at a high risk of osteoarthritis. There are accepted medical tests to identify such patients. For example, association studies have uncovered the genetic factors behind OA, its susceptibility genes, which enables physicians to predict disease occurrence based on genotype information. The predictive assays can screen for a single susceptibility gene, or, more preferably, a combination of susceptibility genes. However, there are few available preventative treatments for patients at risk of developing osteoarthritis.

It would further be advantageous to provide compositions and methods for preventing the onset of osteoarthritis in patients identified as being at risk of developing osteoarthritis.

The present invention provides such compositions and methods.

SUMMARY OF INVENTION

The present invention describes the co-administration of steroids and Zoledronic Acid to prevent or treat osteoarthritis. The steroids can be administered in oral (provided as a gel, capsule, tablet, powder, liquid, or other pharmaceutically acceptable form), intravenous, intramuscular, or inhaled form, as a suppository, or injected directly into a joint.

The co-administration of a steroid decreases the production of cytokines described above, and, therefore, decreases the pro-inflammatory effects of Zoledronic Acid. The co-administration of Zoledronic Acid with steroids treats osteoarthritis, and helps to prevent the onset of osteoarthritis in patients at risk for osteoarthritis.

Existing osteoarthritis treatments are given frequently, for example, daily, or several times a day. In contrast, this combination can be given yearly.

DETAILED DESCRIPTION OF INVENTION

Compositions and methods for treating and preventing osteoarthritis are described. The compositions comprise Zoledronic acid and a steroid.

Zoledronic Acid

In one embodiment, Zoledronic Acid is administered as approved by the FDA, that is, by infusion, typically in 4-5 mg infusions. However, in other embodiments, the Zoledronic Acid is administered by injection.

Zoledronic Acid has a half-life ($t_{1/2\alpha}$) of about 0.24 hours, and its administration is known to be associated with certain side effects in a large sub-population of patients. The co-administration of steroids helps to minimize or eliminate these side effects. By "co-administration," it is meant that the steroids can be administered within two hours before or after the Zoledronic acid, typically within one hour before or after the Zoledronic acid, and, more typically, at the same time, or within a half an hour before or after the Zoledronic Acid.

Steroids

Suitable steroids include, for example, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, aclometasone dipropionate, betamethasone valerate, betamethasone dippropionate, prednicarbate, clobetasone-17-butyrate, clobetasol-17-propionate, fluocortilone caproate, fluocortolone pivalate, and fluprednidene acetate, hydrocortisone-17-butyrate, 17-aceponate, 17-buteprate, and prednicarbate.

The appropriate dose of steroid that is administered can be readily determined by one of skill in the art, for example, a treating physician. However, in one embodiment, the dose of steroids does not exceed the equivalent of 25 mg of prednisolone, and is not less than the equivalent of 5 mg of prednisone.

The steroids can be given orally (for example, 7.5 mg of Prednisone), by a separate infusion (for example, 7.5 mg of Methyl Prednisolone), mixed in with Zoledronic Acid in the same infusion, or be administered intramuscularly, subcutaneously, by rectal suppository, by inhalation, or injected directly into a joint.

Additional Therapeutic Agents

Additional therapeutic agents can be administered with the steroid and Zoledronic Acid. For example, analgesics and anesthetics can be administered. The anesthetic is any compound that is capable of blocking nerve impulses from the area of discomfort to the brain. Representative anesthetics include local anesthetics such as marcaine, procaine (novocaine), chloroprocaine (nesacaine), cocaine, lidocaine, tetracaine (amethocaine, pontocaine), mepivacaine, etidocaine (duranest), bupivacaine (marcaine), dibucaine (cinchocaine, nupercaine), prilocaine (citanest), benzoxinate (dorsacaine), proparacaine (alcaine, opthaine, and opthetic), benzocaine (anesthesin), or butamben (butesin).

The choice of anesthetic will depend on the type of discomfort to be alleviated and is generally known to those skilled in the art of anesthesia. For example, lidocaine and marcaine are commonly injected, along with cortisone or hydrocortisone, directly into joints.

Methods of Treatment

To treat a patient suffering from osteoarthritis, a patient can be administered a combination of Zoledronic Acid and a steroid. The administration can be, for example, once a year.

In one embodiment, the Zoledronic Acid and steroid are administered by simultaneous injection. In one aspect of this embodiment, 7.5 mg of Methyl Prednisolone can be dissolved with about 4-5 mg of Zoledronic Acid in an appropriate vehicle for injection, such as Normal Saline or Phosphate Buffered Saline (up to 100 cc) by swirling gently in room temperature for one minute. This mixture is ideally used within 5 minutes of mixing if kept at room temperature, or within an hour if kept in a refrigerator, so as to minimize the possibility of having a precipitate form.

In another embodiment, a steroid is given orally or via inhalation, and the Zoledronic Acid is given via infusion.

In another embodiment, a mixture of Zoledronic Acid and a steroid is directly injected into a joint, such as a knee, shoulder, or hip joint. In this embodiment, the Zoledronic Acid and steroid can be combined with an anesthetic, or an anesthetic can be administered shortly before or after the combination of the Zoledronic Acid and steroid. Representative anesthetics for this embodiment include lidocaine and Marcaine. Representative steroids for this embodiment include cortisone, hydrocortisone, and pharmaceutically acceptable salts thereof.

Methods for Predicting the Onset of Osteoarthritis

The methods described herein for treating osteoarthritis can also be used to prevent the onset of osteoarthritis for patients at risk of developing osteoarthritis. Numerous methods are described in the literature for predicting osteoarthritis, in man and in other mammals. These methods include, for example, assessments of joint mobility, and genetic testing using known alleles predictive of osteoarthritis.

For example, methods for predicting osteoarthritis of the hip in Labrador retrievers are taught in Corfield, et al., "Assessment of the hip reduction angle for predicting osteoarthritis of the hip in the Labrador Retriever," Aust Vet J. 2007 June; 85(6):212-6.

Methods for predicting osteoarthritis of the hip in humans are taught, for example, in Birrell et al., "Predicting radiographic hip osteoarthritis from range of movement," Oxford Journals Medicine Rheumatology, Volume 40, Issue 5Pp. 506-512. Restriction in range of movement was predictive of the presence of OA in new presenters to primary care with hip pain, and the results of this examination can be used to inform decisions regarding treatment with the methods described herein.

Methods for predicting osteoarthritis of the knee are described, for example, in Takahashi et al., "Prediction model for knee osteoarthritis based on genetic and clinical information," Arthritis Research & Therapy 2010, 12:R187.

Osteoarthritis (OA) is the most common bone and joint disease influenced by genetic and environmental factors. Recent association studies have uncovered the genetic factors behind OA, its susceptibility genes, which enable one to predict disease occurrence based on genotype information. The prediction can be based on the effects of only a single susceptibility gene, or using OA-prediction models based on more than one gene. Risk alleles that can be assessed include the three susceptibility genes, asporin (ASPN), growth differentiation factor 5 (GDF5), and double von Willebrand factor A domains (DVWA).

Clinical information, as well as the number of risk alleles, can be used for OA prediction.

The present invention will be better understood with reference to the following non-limiting examples.

Example 1

Treatment of Osteoporosis Patients with Zoledronic Acid and Steroids

Eight patients with osteoporosis were treated with a single infusion of Zoledronic Acid alone (four patients) or with a single infusion of the combination of prednisone and Zoledronic Acid (ZP, four patients). All four patients who received Zoledronic Acid suffered from PDS. In contrast, none of the patients receiving ZP suffered from PDS.

Of the 8 subjects, five had osteoarthritis. Of these five, three were treated with ZP and two with Zoledronic Acid. All three subjects treated with ZP had a decrease in joint pain (VAS scale) six months after the single infusion and one subject up to one year after the single infusion. In the Zoledronic Acid arm, both subjects had the same (one) or worse (one) level of pain than before the single infusion.

REFERENCES

1. Dicuonzo G, Vincenzi B, Santini D et al. Fever after Zoledronic acid administration is due to increase in TNF-alpha and IL-6. J Interferon Cytokine Res 2003; 23: 649-654.
2. Schweitzer D H, Oostendorp-van de Ruit M, Van der Pluijm G et al. Interleukin-6 and the acute phase response during treatment of patients with Paget's disease with the nitrogen-containing bisphosphonate dimethyl-amin hydroxyl-propylidene bisphosphonate. J Bone Miner Res 1995; 10: 956-962.
3. Thiebaud D, Sauty A, Burckhardt P et al. An in vitro and in vivo study of cytokines in the acute-phase response associated with bisphosphonates. Calcif Tissue Int 1997; 61: 386-392.
4. Mariani S, Muraro M, Pantaleoni F, Fiore F, Nuschak B, Peola S, et al. Effector T cells and tumor cells as immune targets of Zoledronic acid in multiple myeloma. Leukemia 2005; 18: 139-45.
5. Masoodi, Nasseer A. Oral Bisphosphonates and the Risk for Osteonecrosis of the Jaw. BJMP 2009:2(2) 11-15. June 2009).
6. Woo S B, Hellstein J W, and Kalmar J R. Systemic Review: Bisphosphonates and osteonecrosis of the jaws. Ann Intern Med 2006; 144:753-6
7. Wilkinson G S, Kuo Y F, Freeman J L, Goodwin J S. Intravenous bisphosphonate therapy and inflammatory conditions or surgery of the jaw: a population based analysis. J Natl Cancer Institute 2007 Jul. 4; 99(13):1016-24.
8. Corfield, et al. Assessment of the hip reduction angle for predicting osteoarthritis of the hip in the Labrador Retriever. Aust Vet J. 2007 June; 85(6):212-6.
9. Birrell et al. Predicting radiographic hip osteoarthritis from range of movement. Oxford Journals Medicine Rheumatology, Volume 40, Issue 5Pp. 506-512.
10. Takahashi et al. Prediction model for knee osteoarthritis based on genetic and clinical information. Arthritis Research & Therapy 2010, 12:R187

The contents of all references described herein are incorporated herein by reference in their entirety for all purposes.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed:

1. A method of treating osteoarthritis, the method comprising administering a combination of Zoledronic Acid and a steroid to a patient in need of treatment or prevention thereof.

2. The method of claim 1, wherein the method involves treating a patient suffering from osteoarthritis.

3. The method of claim 1, wherein the method involves administering the combination to a patient with risk factors indicating that they are or will be suffering from osteoarthritis.

4. The method of claim 1, wherein the Zoledronic Acid is given via infusion or subcutaneously or orally or intramuscularly, and the steroid is given during, or between fifteen minutes and an hour before or after the Zoledronic Acid infusion.

5. The method of claim 1, wherein the Zoledronic Acid is given via infusion or subcutaneously or orally or intramuscularly, and the steroid is given around between a half hour before and a half hour after the Zoledronic Acid infusion.

6. The method of claim 1, wherein the steroid is given orally, intravenously, subcutaneously, intramuscularly, by inhalation, by injection into a joint, or by a rectal suppository.

7. The method of claim 1, wherein the dose of the steroid is equivalent to between 5 mg and 25 mg of prednisone.

8. A composition comprising methyl prednisolone and Zoledronic Acid in a pharmaceutically acceptable solution for intravenous administration.

9. The composition of claim 8, wherein the solution is selected from the group consisting of saline and phosphate buffered saline.

10. The composition of claim 8, wherein the combined amount of prednisolone and Zoledronic Acid is between about 5 and 30 mg.

11. The composition of claim 10, wherein 4 or 5 mg Zoledronic Acid is dissolved with 5 to 25 mg prednisolone in Normal Saline for intravenous infusion to treat osteoarthritis.

12. A method for treating osteoarthritis in a joint of a host, comprising administering a combination of a steroid and Zoledronic Acid directly into the joint in the host, with or without an anesthetic.

13. The method of claim 12, wherein the joint is any joint including but not limited to knee, shoulder, hip, carpal, metacarpal, interphalengeal, tarsal, metatarsal, elbow, ankle, vertebral, or facetal joint.

14. The method of claim 12, wherein the steroid is cortisone or hydrocortisone, or a pharmaceutically-acceptable salt thereof.

15. The method of claim 12, wherein the anesthetic is lidocaine, Marcaine, a pharmaceutically-acceptable salt thereof, or a mixture thereof.

* * * * *